United States Patent [19]

Gramer

[11] Patent Number: 5,459,140
[45] Date of Patent: Oct. 17, 1995

[54] COMBINATION PREPARATION BASED ON DIPIVALYLEPINEPHRINE (DPE) FOR REDUCING INTRAOCULAR PRESSURE

[76] Inventor: Eugen Gramer, An den Muhltannen 16, 8700 Würzburg, Germany

[21] Appl. No.: 4,842

[22] Filed: Jan. 19, 1993

[30] Foreign Application Priority Data

Jan. 17, 1992 [DE] Germany .................. 42 01 079.9

[51] Int. Cl.⁶ .................. A61K 31/135; A61K 31/535; A01N 37/12
[52] U.S. Cl. .................. 514/236.2; 514/551; 514/649; 514/912; 514/913; 514/963; 514/965
[58] Field of Search .................. 424/423, 426, 424/427, 428, 434, 435, 499, 501, 78.03, 78.04, 78.33; 514/912, 913, 963, 965, 395, 649, 236.2, 551; 523/122

[56] References Cited

U.S. PATENT DOCUMENTS

| | | | |
|---|---|---|---|
| 4,801,617 | 1/1989 | LeClerc et al. | 514/392 |
| 4,897,412 | 1/1990 | LeClerc et al. | 514/401 |
| 4,904,649 | 2/1990 | Schwartz | 514/171 |
| 4,906,467 | 3/1990 | Schwartzman et al. | 514/560 |
| 5,173,298 | 12/1992 | Meadows | 424/427 |
| 5,212,168 | 5/1993 | Schwartz | 514/179 |

FOREIGN PATENT DOCUMENTS

89/10120  11/1994  WIPO.

*Primary Examiner*—Thurman K. Page
*Assistant Examiner*—Carlos Azpuru
*Attorney, Agent, or Firm*—John F. A. Earley; John F. A. Earley, III

[57] ABSTRACT

A preparation for reducing intraocular pressure consisting essentially of a therapeutically effective amount of the fixed combination of dipivalylepinephrine and carbachol (preparation 1) or dipivalylepinephrine and beta-blocker (preparation 2). The preparations may be prepared both as a solution and as a suspension. Either preparation is administered twice daily.

4 Claims, No Drawings

COMBINATION PREPARATION BASED ON DIPIVALYLEPINEPHRINE (DPE) FOR REDUCING INTRAOCULAR PRESSURE

The present invention pertains to a combination preparation based on DPE for topical treatment on the eye for reducing the pathologically increased intraocular pressure in glaucoma. Dipivalyl epinephrine (DPE) is a component of the German drugs D-Epifrin 0.1%® and Glaucothil 0.1%® and is a component of the combination preparations Thiloadren® and Thilodigon 0.5%® (German Patent No. DE 30,33,898 C2). The combination preparation according to the present invention needs to be applied only twice a day (in the mornings and evenings), and contains carbachol or a beta-blocker (beta-1-beta-2-blocker or selective beta-1-blocker) as its second active ingredient component.

State of the Art

The following combination preparations have been known to date:
Direct parasympathomimetic/direct sympatholytic
pilocarpine 2% and metipranolol 0.1% (Normoglaucon®)
pilocarpine 2% and timolol 0.5% (Timpilo®)
Direct parasympathomimetic/direct sympathomimetic
pilocarpine 1% and dipivalyl epinephrine 0.1% (Thiloadren®)
pilocarpine 2% and epinephrine 2% (Piladren®)
Indirect sympatholytic/direct sympathomimetic
guanethidine 0.5% and dipivalyl epinephrine 0.1% (Thilodigon® 0.5%)
guanethidine 1% and epinephrine 0.2% (Suprexon®)
guanethidine 3% and epinephrine 0.5% (Suprexon®)
Direct parasympathomimetic/reversible cholinesterase inhibitor
pilocarpine 2% and neostigmine 1% (Syncarpin®)
pilocarpine 2% and physostigmine 0.25% (Isopto-Pilomin®)
pilocarpine 2% and physostigmine 0.5% (Pilo-Eserina).

Consequently, the basic task of the present invention is to provide combination preparations with which intensified reduction in the intraocular pressure can be achieved compared with the administration of the individual preparations. This task is accomplished as shown in the claims below. Handling is simplified in the case of the preparation according to the present invention (only one vial), and the risk of incorrect use is reduced, and this preparation (preparation I) can thus also be used in the case of glaucoma with narrow iridocorneal angle due to the preponderance of the miotic effect, without the risk of an attack of glaucoma. Due to this fixed combination, it has now become possible, for the first time ever, to use DPE preparations even in the case of narrow iridocorneal angle. Carbachol, a direct parasympathomimetic with simultaneous cholinesterase inhibition, has been selected in preparation I, because it has a longer duration of action and brings about a greater reduction in the intraocular pressure than do other miotics, e.g., pilocarpine, and the carbachol-DPE combination preparation is therefore more likely (especially when used in the form of a suspension), in principle, to guarantee a reduction in the frequency of applications to twice a day at constant reduction in the intraocular pressure.

On the advantages of carbachol in combination preparations (cf. PCT/EP 91/01295).

The combination preparation according to the present invention consists of a combination of the following classes of active ingredients:

Combination Preparation I
Direct parasympathomimetic with simultaneous cholinesterase inhibition/direct sympathomimetic carbachol (solution or suspension) 3% or less and DPE (dipivalyl epinephrine 0.1%)

Example
(A) Composition of a solution
  carbachol eye drops 3%
  dipivalyl epinephrine 0.1%
  preservative: benzalkonium chloride.
(B) Composition of a suspension
  carbachol eye drops 3%
  dipivalyl epinephrine 0.1%
  preservative: benzalkonium chloride.

Combination Preparation II
Direct sympathomimetic/direct sympatholytic dipivalyl epinephrine 0.1% or less (lower limit: 0.09%) and beta-blocker, e.g., betaxolol-S 0.28% or nonselective beta-1-beta-2-blocker (suspension) or: dipivalyl epinephrine 0.1% or less (lower limit: 0.09%) and beta-blocker, e.g., betaxolol 0.5% (solution) or nonselective beta-1-beta-2-blocker.

EXAMPLES dipivalyl epinephrine 0.09% with betaxolol suspension 0.28% or betaxolol solution 0.5%.
Dipivalyl epinephrine 0.1% (lower limit: 0.09%) with one of the following beta-blockers as a solution:
  befunolol 0.5% or 0.25% as the lower limit
  levobunolol 0.5% or 0.25% as the lower limit
  pindolol 0.5% or 0.25% as the lower limit
  timolol 0.5 or 0.25% as the lower limit
  carteolol 2% or 1% as the lower limit
  metipranolol 0.3% or 0.1% as a solution.

If the suspension form is used, the concentration can be reduced within the said limits, to half as a maximum, at equal reduction in pressure.

The two combination preparations based on DPE may be prepared as a solution or as a suspension. The suspension form in a combination preparation leads, for both substances (components), to better penetration and slower release of the active ingredient (the bolus character of the drugs is eliminated), and thus in turn to higher bioavailability with a higher probability of a constant reduction in intraocular pressure with only two applications daily, which makes it possible to reduce the concentrations of the individual substances, without limiting the duration of action and the intensity of action compared with the free combination of the individual substances.

The pharmacokinetics of combination preparation II, which contains a beta-blocker component, is different due to the reduction in aqueous humor production brought about by the beta-blocker, and the bioavailability of the DPE component is therefore also longer, which may make it possible to reduce the concentration of the DPE component or of both components at equal duration of action and equal intensity of action, with only two daily applications of the combination preparation. The combination preparation II can be prepared, in principle, with a beta-1-selective beta-blocker (which is theoretically more suitable), or with any nonselective beta-1-beta-2-blocker. The beta-blocker is selected depending on the beta-blocker approved for use in the eye, with which, together with DPE, the best result in terms of stability and pH value is reached in the case of the fixed combination (the pH value is decisive for penetration and local tolerance). Good additive intraocular pressure-reducing effect can be achieved in humans with a free combination of nonselective beta-blockers with DPE, so that the practical relevance of the use of a beta-1-selective beta-blocker in humans cannot yet be definitively addressed in the case of a DPE-beta-blocker combination preparation. It is decisive that only the prodrug of epinephrine, namely, DPE, is used as the epinephrine component, because it has milder local and systemic side effects than other epinephrine components at equal reduction in the intraocular pressure.

Since a drug inhibiting the production of aqueous humor and a drug improving the discharge of aqueous humor are combined in preparation II, the pharmacokinetics will change, so that the concentration of DPE can be reduced from 0.1% to 0.09% at equal pressure-reducing effect.

The fixed combination of the individual components in combination preparations leads to a longer duration of action and causes a greater reduction in pressure compared with the free combination of the individual substances. The action mechanism of the combination preparations therefore seems to be not only the sum of the individual mechanisms of the individual preparations, which is a surprising phenomenon for which there is no ascertained pharmacologic explanation so far. The more sustained and increased pressure-reducing effect of the combination preparations can be explained not only by a reduction in the mutual wash-out effect, but a change in pharmacokinetics and/or another interaction of the drugs in the eye can be suspected as well. If the suspension form is used, a reduction in the total amount of active ingredient can be achieved, as a result of which a higher safety profile is obtained in terms of systemic and local side effects. This suspension form consists of 2.5 mg poly(styrenedivinylbenzene)sulfonic acid (Amberlite IRP-69) as the active ingredient carrier and 2 mg Carbomer 934 P to increase the depot function. How far the amount of the active ingredient can be reduced while maintaining the two daily applications at equal reduction in the intraocular pressure must be checked in animal experiments for the individual combination preparations I and II; reduction in the active ingredient concentration is ensured in the case of the beta-blocker component from 0.5% in the solution to 0.28% in the suspension at equal pressure-reducing effect.

One decisive advantage of the combination preparation according to the present invention is application only twice a day with both the aqueous solution and the suspension. This leads to a simpler therapy protocol and consequently to an improvement in compliance at prolonged duration of action and more intense pressure reduction compared with the free combination of the individual substances. In the case of the carbachol-DPE combination preparation, the frequency of applications is reduced to two daily applications of the combination preparation at equal pressure-reducing effect of carbachol 3% (three times a day) and the beta-blocker (twice a day). Carbachol combination preparations are the only miotic combination preparations with which a constant reduction in the intraocular pressure can be expected with two daily applications even in the case of higher intraocular pressure values. The dual action of carbachol as a direct parasympathomimetic and as a cholinesterase inhibitor is therefore advantageous in a fixed combination with beta-blockers (PCT/EP 91/01295) as well as in a fixed combination with dipivalyl epinephrine (DPE). In the carbachol-DPE combination preparation, the two components exert discharge-improving effect at different sites of action, which directly counteracts the pathogenesis of the increase in the intraocular pressure (progression of discharge).

The value of carbachol, this old substance, as a component of a miotic-DPE combination within a combination preparation that needs to be applied only twice a day, and its marked advantages over the pilocarpine-beta-blocker combination, e.g., Normoglaucon® or the pilocarpine-DPE combination, e.g., Thiloadren® (frequency of applications: three times a day because of the short duration of action of the pilocarpine component compared with that of carbachol 3%), are due to the pharmacokinetics of this substance. In the combination preparation I according to the present invention, DPE can be used only in a combination of 0.1% or less, and in the fixed combination with carbachol 3%, it can also be used in the case of narrow iridocorneal angles, without requiring prior surgical peripheral iridectomy.

The new combination preparations can extend the scale of a combination drug therapy with good compliance, and represent a medical and ethical necessity in light of the increasing life expectancy of the population.

The concentration of dipivalyl epinephrine in the preparation according to the present invention is preferably 0.1–0.09%, the concentration of carbachol is 3–1.5%, and that of the beta-blocker is 0.5–0.25%.

I claim:

1. Preparation for reducing intraocular pressure consisting essentially of a therapeutically effective amount of the fixed combination of dipivalylepinephrine and carbachol for those in need thereof.

2. Preparation in accordance with claim 1, characterized in that the dipivalyl epinephrine is present at a concentration of 0.1–0.09%.

3. Preparation in accordance with claim 2, characterized in that the carbachol is present at a concentration of 3–1.5%.

4. Preparation for reducing intraocular pressure consisting essentially of a therapeutically effective amount of the fixed combination of dipivalylepinephrine and a beta-1-beta-2-blocker for those in need thereof.

* * * * *